United States Patent
Antaki et al.

[11] Patent Number: 5,888,242
[45] Date of Patent: Mar. 30, 1999

[54] SPEED CONTROL SYSTEM FOR IMPLANTED BLOOD PUMPS

[75] Inventors: James F. Antaki, Allison Park; Seongjin Choi, Pittsburgh; John Robert Boston, Wexford, all of Pa.; Kenneth C. Butler; Douglas C. Thomas, both of Carmichael, Calif.

[73] Assignee: Nimbus, Inc., Rancho Cordova, Calif.

[21] Appl. No.: 740,749

[22] Filed: Nov. 1, 1996

[51] Int. Cl.[6] .................................................. A61M 1/10
[52] U.S. Cl. ............................. 623/3; 604/66; 604/67; 604/50
[58] Field of Search ...................... 600/16, 17; 604/13, 604/65, 66, 67, 92.1, 19, 118, 151; 417/1, 14; 415/206; 623/3

[56] References Cited

U.S. PATENT DOCUMENTS

| | | | |
|---|---|---|---|
| 5,693,091 | 12/1997 | Larson, Jr. et al. | 623/3 |
| 5,722,930 | 3/1998 | Larson, Jr. et al. | 600/16 |

OTHER PUBLICATIONS

"In Search of Chronic Speed Control for Rotary Blood Pumps"–Article which appeared in the Proceedings of the Waseda International Congress of Modeling and Simulation Technology for Artificial Organs in Tokyo, Japan on 01–03 Aug. 1996; author J.F. Antaki, S. Choi, D. Amin, J.R. Boston, Y.–C. Yu, J.P. Kerrigan, H. Konishi, P. Litwak, H.S. Borovetz, D. Thomas and B.P. Griffith.

*Primary Examiner*—Wynn Wood Coggins
*Assistant Examiner*—N. Kent Gring
*Attorney, Agent, or Firm*—Harry G. Weissenberger

[57] ABSTRACT

An automatic speed control system continually adjusts the speed of an implanted cardiac assist blood pump to an optimum level for the varying physiological needs of the patient. It does this by periodically iteratively incrementing the speed setpoint of the pump. When the system detects the imminence of a ventricular collapse at diastole, it decrements the speed setpoint by a predetermined safety margin. An alarm condition is provided if the setpoint decrease results in an insufficient blood flow rate through the pump. The flow rate and imminence of ventricular collapse are computed in real time as functions of only the pump's motor current and speed setpoint.

22 Claims, 5 Drawing Sheets

SPEED CONTROL SYSTEM FOR IMPLANTED BLOOD PUMPS

FIELD OF THE INVENTION

The present invention relates to implanted blood pump systems, and more particularly to adaptive speed control for continuously driven blood pumps so as to automatically regulate the speed of the pump in accordance with the physiological needs of the patient.

BACKGROUND OF THE INVENTION

Implantable blood pumps for chronic left ventricular assist have been and are being developed in a number of forms. For example, an implantable, transcutaneously powered electric axial flow pump is shown in application Ser. No. 08/424,165 entitled Implantable Electric Axial-Flow Blood Pump. Inasmuch as the blood flow requirements of the human body vary substantially and unpredictably with posture, stress, activity, ambient temperature and other physiological and psychological factors, it is necessary to continually adapt the pump's flow rate to the patient's needs.

Two factors limit the usable speed range of, e.g., the axial flow pump of Ser. No. 08/424,165. At the lower end, the speed must be sufficient to produce enough blood flow to deliver essential substances to the vital issues and remove products of metabolism, as well as cool the bearings and prevent thrombus formation. At the upper end, the pump speed must not be so high as to produce a zero or negative pressure within the inlet during diastole (i.e. it must never cause suction in the ventricle). The pump is most effective when operating close to the upper end of the range.

In an ambulatory patient, it is not practical to directly measure the pressure and flow rate information necessary for pump control, because the necessary sensors would complicate the pump's electronics and present unnecessary failure risks.

It has previously been hypothesized, as pointed out in the article entitled "In Search of Chronic Speed Control for Rotary Blood Pumps" in the Proceedings of the Waseda International Congress of Modeling and Simulation Technology for Artificial Organs in Tokyo, Japan on 01–03 Aug. 1996, that the pump motor current, voltage and speed may contain information from which pressures and flow rates may be determined. However, no practical way of evaluating that information in real time and putting it to use in a physiological environment has been determined to date.

SUMMARY OF THE INVENTION

The invention provides an automatic, physiologically driven speed control for an implanted rotary or other continuously driven electric blood pump which continually adjusts the pump speed in real time to produce an optimum blood flow rate through a wide range of short-term and long-term changes in the patient's physiology, using only the current and speed of the pump motor as measured control parameters.

Basically, the system of this invention consists of a brushless, electronically commutated DC motor whose rotor is part of the pump rotor, and whose speed is conventionally controlled, in accordance with a setpoint signal provided by a microprocessor, by a switching network responsive to the motor's back electromagnetic force (BEMF). The microprocessor periodically increments that setpoint signal iteratively until it detects the imminence of a ventricular collapse, and then decrements the setpoint signal slightly. Consequently, the pump always operates at the optimum speed for the patient's physiological requirements at any given time i.e. at the limit of venous return (the imminence of suction). In more formal terms of optimal control theory, this operation can be expressed as minimize {atrial pressure}
subject to:
  atrial pressure>threshold-1 (approx. +)
  arterial pressure>threshold-2
  flow >threshold-3 wherein "ventricular diastolic pressure" could be substituted for "atrial pressure" if desired, and wherein threshold-2 is a function of flow.

The detection of an imminent ventricular collapse (i.e. ventricular suction at diastole) can be done in several ways by monitoring the pump motor current draw. In a first embodiment of the invention, the cyclical current fluctuations during the systole-diastole cycle are monitored. It has been empirically determined that a detectable current spike occurs just prior to a ventricular collapse caused by suction. Consequently, the detection of this current spike can be used to reduce the pump speed to a safe value.

In another embodiment of the invention, advantage is taken of the fact that the mean flow rate increases at an incrementally decreasing rate as pump speed is increased. Consequently, the derivative of the flow rate (in accordance with the invention, the flow rate can be calculated in real time from the motor current) with respect to speed (i.e. the setpoint signal) can be used as a speed reduction signal when the derivative drops below a predetermined minimum.

Finally, in a third embodiment of the invention, it has been found that the second harmonic of the current fluctuation during a heartbeat cycle increases substantially shortly before ventricular collapse occurs. Thus, a spectral analysis representation of the time-current wave form during the heartbeat cycle can be continuously computed, and a speed reduction signal can be generated when the second harmonic term of the series exceeds a predetermined threshold.

On the other end of the operational range, an alarm signal can be generated when the flow rate drops below a preset minimum necessary for the safe operation of the pump. As pointed out above, the flow rate can be continually calculated in real time in accordance with the invention, knowing the motor current and speed setpoint.

By the use of the invention, the pump speed can be continually adjusted to an optimal level not only in response to transient changes in the patient's physiology, but also in response to long-term changes such as the patient's recovery from heart disease.

DESCRIPTION OF THE PREFERRED EMBODIMENT

Figure 1:
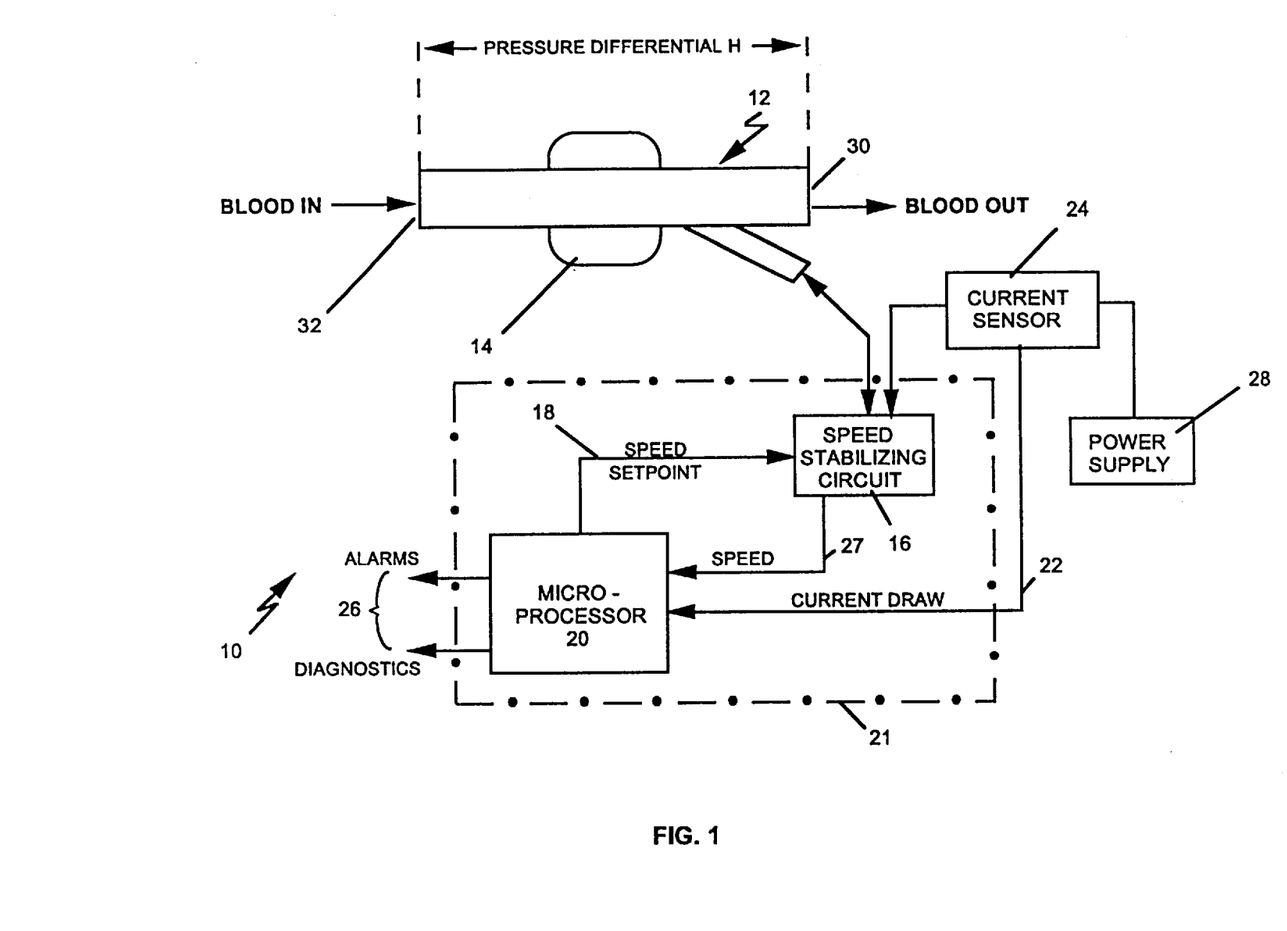
FIG. 1 is a block diagram illustrating the inventive system.
Figure 2:
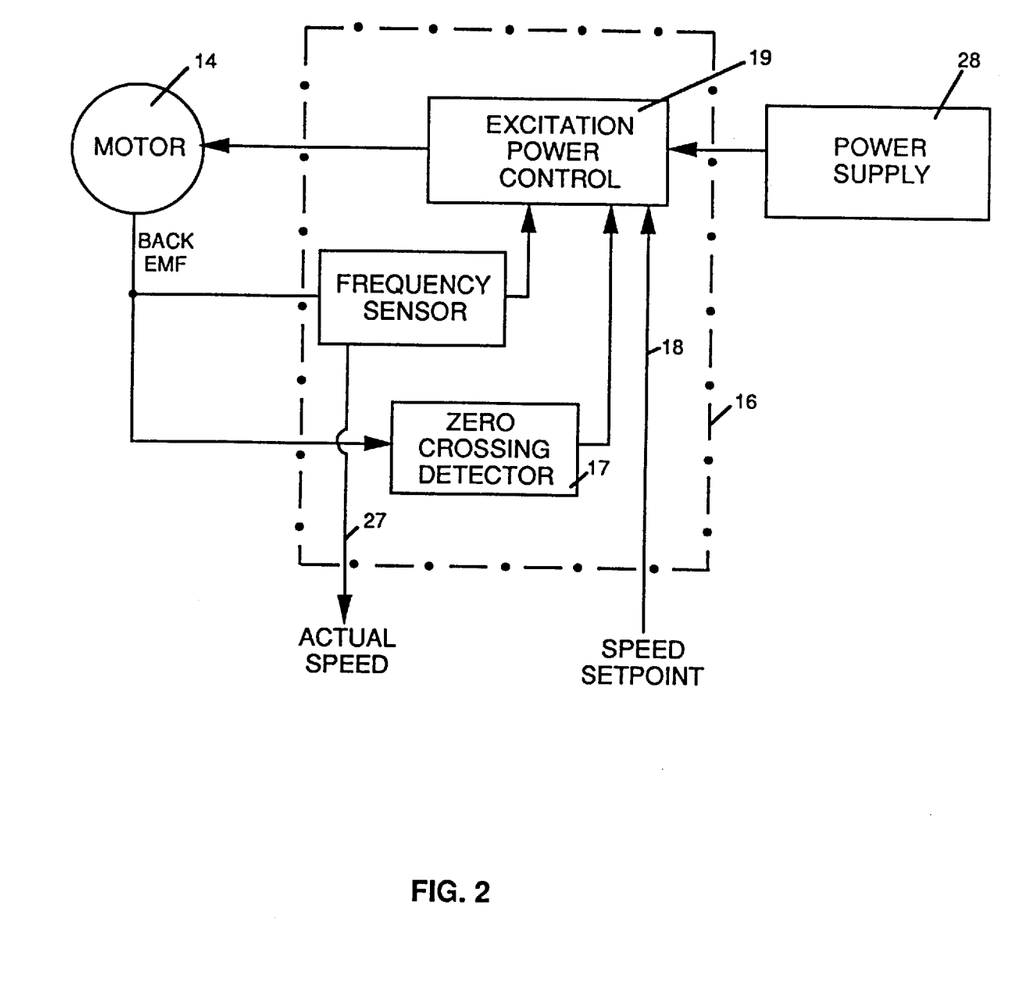
FIG. 2 is a block diagram of the speed stabilizing circuit.

FIG. 1 shows the system 10 to include an implanted axial flow blood pump 12 (the principles of this invention are equally applicable to other types of blood pumps such as centrifugal pumps) driven by a brushless DC motor 14. The speed of the motor is maintained, by a speed stabilizing circuit 16, at a level dictated by the setpoint signal 18. The speed stabilizing circuit 16 (FIG. 2) is microprocessor based and is responsive to the back electromotive force (BEMF) generated by the motor. A zero crossing detector 17 detects the zero crossings of the BEMF curve and applies an indication thereof to the excitation power control 19. The control 19 uses the BEMF and the timing of the zero crossing of the BEMF as control parameters to adjust the motor excitation power. The speed stabilizing microprocessor 16 can be integrated with the speed control microprocessor 20 into a single microprocessor 21 (FIG. 1).

The setpoint signal 18 is produced by a microprocessor 20 whose sole input variable is the motor current draw signal 22 produced by current sensor 24. The microprocessor 20 may conveniently have alarm and diagnostic outputs 26 through which the operation of the system can be observed, and alarm indications or remedial action such as defibrillation can be initiated. The operation of the microprocessor 20 is described in more detail below.

Two parameters are known to the microprocessor 20 without the use of any sensors: a) the pump speed co (speed signal 27) ; and b) the current I (current signal 22) drawn by the motor 14.

The dynamics of a three-winding brushless DC motor such as the motor 14 can be described as $$J\, d\omega/dt = T_e - B\omega - T_p \quad (1)$$

and $$T_e = K_B \sin(\theta) i_a + K_B \sin(\theta - 2\pi/3) i_b + K_B \sin(\theta - 2\pi/3) i_c \quad (2)$$

wherein $i_a$, $i_b$ and $i_c$ are the phase currents in the three windings, $\omega$ is the rotor speed, $\theta$ is the angular position of the rotor, J is the inertia of the rotor, B is the damping coefficient, $K_B$ is the back EMF constant, $T_e$ is the motor torque, and $T_p$ is the load torque on the pump 12.

Because the motor 14 has a sinusoidal back EMF, the phase currents also have a sinusoidal wave form. Consequently, the motor torque $T_e$ can be expressed simply as $$T_e = 3/2 K_B I \quad (3)$$

wherein I is the sum of the phase currents. Applying formula (3) to formula (1), we find that $$J\, d\omega/dt = 3/2 K_B I - B\omega - T_p \quad (4)$$

The load torque Tp is in turn expressible as $$T_p = a_0 \omega^3 + a_1 Q \omega^2 \quad (5)$$

in which $a_0$ and $a_1$ are empirically determined coefficients for a given pump 12, and Q is the blood flow rate through the pump 12. Combining equations (4) and (5), we find that $$J\, d\omega/dt = 3/2 K_B I - B\omega - (a_0 \omega^3 + a_1 Q \omega^2) \quad (6)$$

The terms of equation (6) can now be transposed to solve for Q as a function of I and $\omega$:

$$Q = \frac{\frac{3}{2} K_B I - B\omega - \left(a_0 \omega^3 + J \frac{d\omega}{dt}\right)}{a_1 \omega^2} \quad (7)$$

in which J, $K_B$, B, $a_0$ and $a_1$ are all constants for a given pumpmotor 14; $\omega$ is represented by the speed signal 18 of FIG. 1, i.e. an input of microprocessor 20; and I is the only measured variable input applied to the microprocessor 20.

One of the limit parameters of the pump 12 is the minimum blood flow Q which the pump 12 can sustain without risking mechanical and/or physiological damage. Consequently, if a decrease in the speed setpoint signal 18 causes Q to drop to, e.g., 5 l/min., the microprocessor must not reduce the speed setpoint any further, and an alarm condition is present.

The other limit parameter for the pump 12 is the avoidance of left ventricular suction, i.e. the avoidance of any condition in which the pressure at the inlet 32 of the pump 12 (or, more accurately, the pressure at the tip of the inlet cannula of the pump 12 which protrudes into the left ventricle) goes negative at diastole. Inasmuch as that pressure is not known without a sensor, the microprocessor 20 must determine the imminence of such a condition internally or from the current input 22 alone.

Because it is physiologically desirable to operate the pump 12 at a level at which the inlet pressure at diastole is slightly above zero, the microprocessor 20 is programmed to continually, e.g. every ten seconds or so, or perhaps after each twelfth or so heartbeat (heartbeats can be identified by the cyclical variations of I between systole and diastole), increase the speed setpoint and look for signs of imminent ventricular collapse (i.e. ventricular suction), then reduce the setpoint slightly. In that manner, the microprocessor 20 can continually adjust the pump speed in real time to its optimum level for the patient's varying physiological demands.

Figure 3:
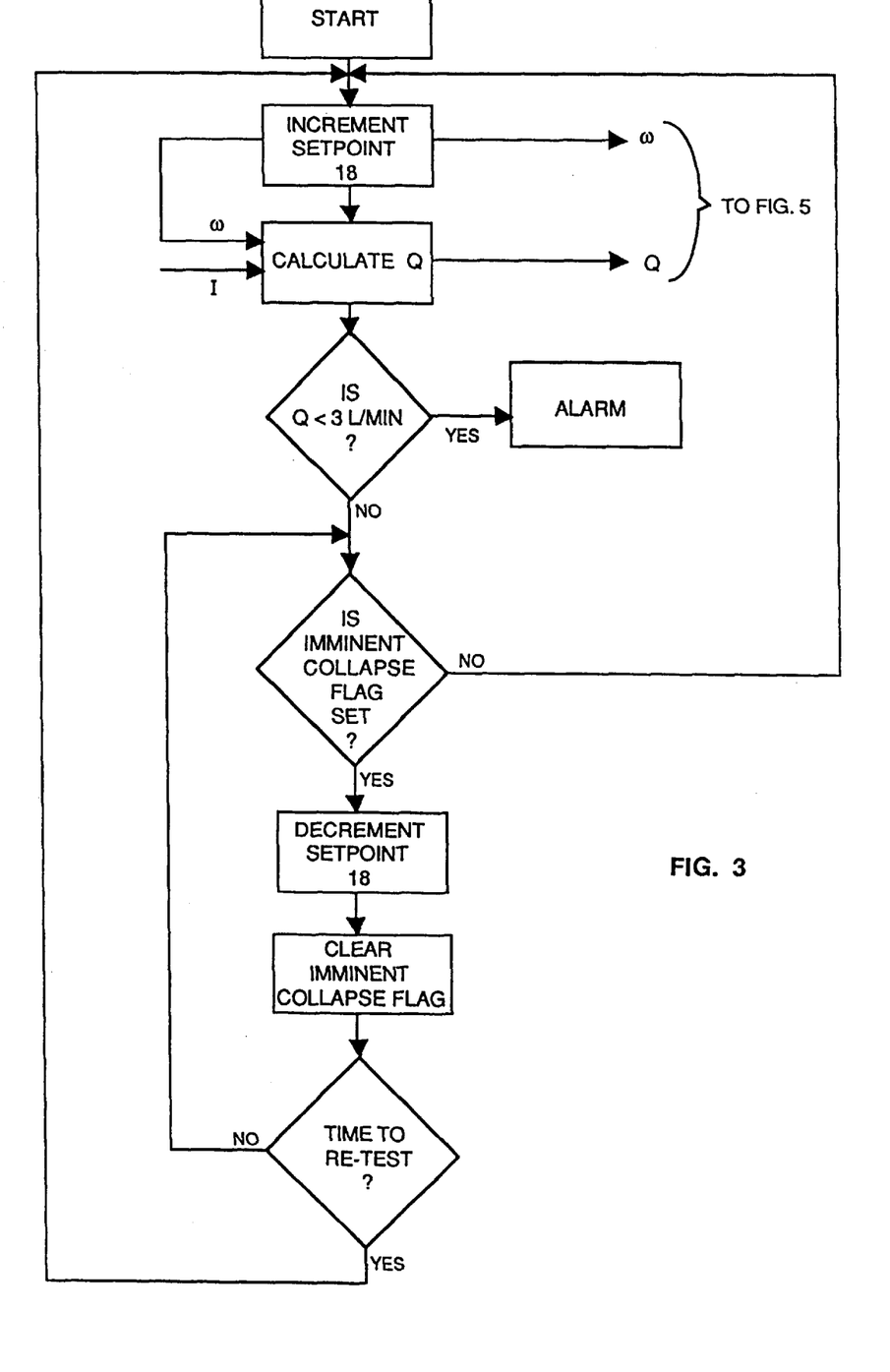
FIG. 3 is a flow chart of the control microprocessor's main routine.

FIG. 3 depicts, in flow chart form, the foregoing mode of operation of microprocessor 20. As shown in that figure, the microprocessor periodically, at the appropriate time intervals mentioned above, computes the blood flow rate Q and tests the maximum speed at which the pump 12 can be operated without causing ventricular collapse. It looks continuously, however, for signs of imminent ventricular collapse, so that if one occurs between computation cycles, the pump speed will immediately be decremented to a safe value.

Inasmuch as provisions can be made in the microprocessor 20 to vary the test time interval and the amount of decrementation following the detection of an imminent ventricular collapse, the system of this invention can be made to allow the cardiologist to gradually wean the patient's heart from the blood pump 12 as the heart's health improves. For this purpose, the decrementation and test interval can be increased (as long as the decrementation is not so large as to cause the insufficient flow alarm condition) so as to make the heart operate at a higher pressure for longer intervals.

Figure 4:
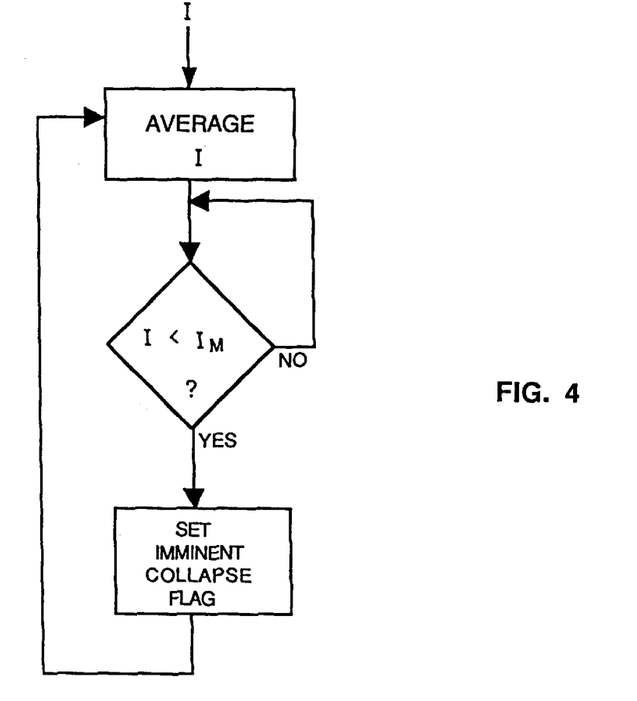
FIG. 4 is a flow chart illustrating two embodiments of an imminent ventricular collapse flagging routine.

The detection of imminent ventricular collapse can be done in a variety of ways exemplified by the four preferred embodiments of the invention. In the first embodiment (FIG. 4), advantage is taken of the fact that the motor current I normally tracks the flow rate Q quite consistently, but spikes noticeably in the negative direction at diastole when the inflow pressure approaches zero, i.e. when the outflow demand starts to exceed inflow supply. Consequently, the detection in the first embodiment is done by averaging the motor current and setting an imminent collapse flag when the flow (and hence the current) momentarily drops below that average by more than a predetermined adaptive threshold amount $I_M$.

Figure 5:
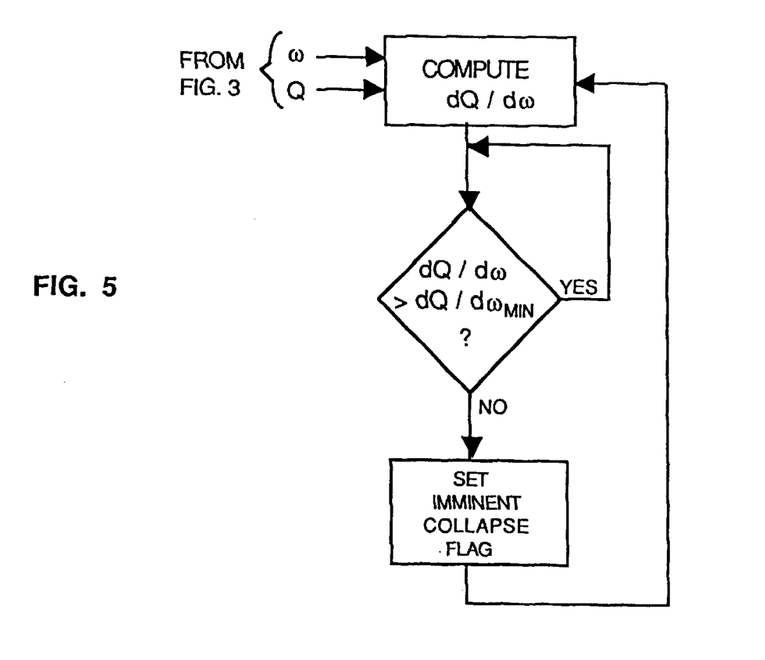
FIG. 5 is a flow chart illustrating a third embodiment of an imminent ventricular collapse flagging routine.

In a second embodiment of the invention (FIG. 5), advantage is taken of the fact that with increasing pump speed, the mean blood flow rate through the pump 12 should increase at an incrementally decreasing rate. When the patient's venous return is matched by the pump 12, this rate becomes zero. Because ventricular suction may occur prior to that point, an empirically determined minimum rate of flow increase with speed increase is advantageously set to trigger the flag; in other words, the flag is set when $dQ/d\omega < dQ/d\omega MIN$.

Figure 6:
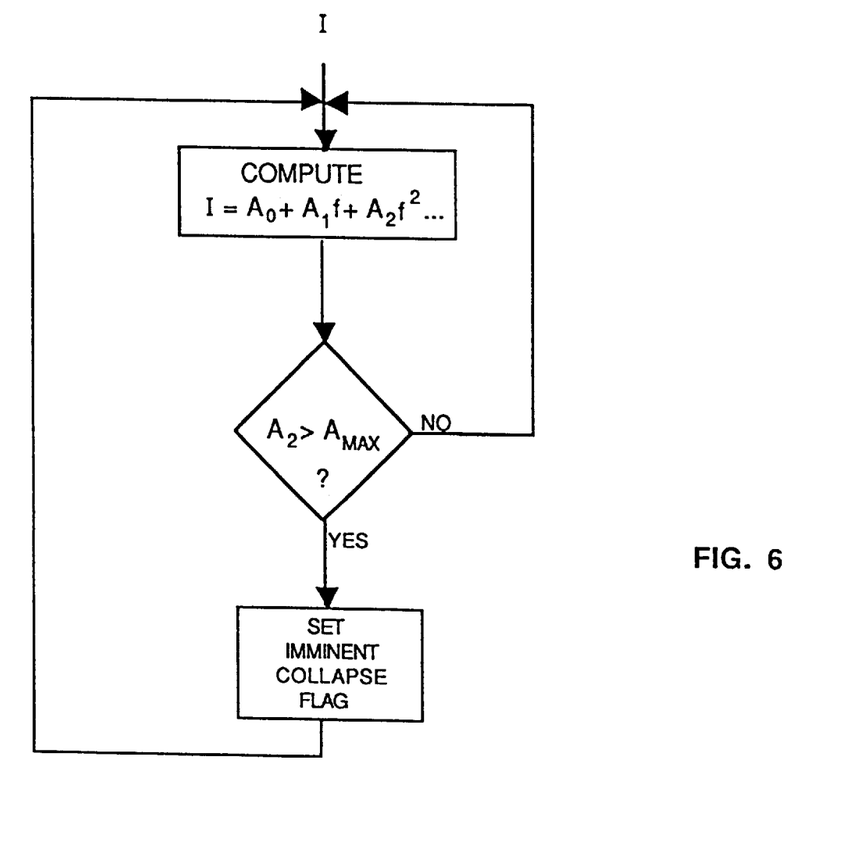
FIG. 6 is a flow chart illustrating a fourth embodiment of an imminent ventricular collapse flagging routine.

In the third embodiment of the invention (FIG. 6), advantage is taken of the empirically discovered fact that the second harmonic component of the motor current waveform over a heartbeat cycle rises substantially as the pump speed approaches the ventricular collapse danger point. Consequently, another way of detecting imminent collapse is to compute a spectral analysis of the motor current I with the heartbeat frequency f as the fundamental frequency, and to trigger the imminent collapse flag when the second harmonic coefficient $A_2$ exceeds a predetermined value $A_{MAX}$.

It should be understood that the exemplary speed control system for implanted blood pumps described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. A method of automatically controlling the speed of a continously driven rotary implanted electric chronic heart assist blood pump in accordance with the patient's time-varying physiological requirements, comprising the steps of:

a) periodically incrementing pump speed;

b) detecting the imminence of ventricular collapse; and c) decrementing pump speed by a predetermined amount whenever said imminence is detected.

2. The method of claim 1, in which said periodic pump speed incrementing step is performed at substantially ten-second intervals.

3. The method of claim 1, in which said periodic pump speed incrementing step is performed substantially every dozen heartbeats of the patient.

4. The method of claim 1, in which said detecting step includes:

i) measuring the current drawn by the motor of said blood pump;

ii) computing the blood flow rate through said pump from said current measurement;

iii) computing the derivative of said flow rate with respect to pump speed; and iv) providing a detection indication when said derivative drops below a predetermined minimum value.

5. The method of claim 4, in which said flow rate is computed from said current measurement by the formula $$Q = \frac{\frac{3}{2} K_B I - B\omega - \left( a_0 \omega^3 + J \frac{d\omega}{dt} \right)}{a_1 \omega^2}$$

wherein Q is the flow rate; I is the motor current; $\omega$ is the pump speed; and $K_B$, B, J, $a_0$ and $a_1$ are constants associated with said pump and motor.

6. The method of claim 1, in which said detecting step includes:

i) measuring the current drawn by the motor of said pump;

ii) computing the derivative of said current with respect to speed as the speed of said pump is varied; and iii) providing a detection indication when said derivative exceeds a predetermined level.

7. A method of automatically controlling the speed of a continuously driven implanted electric chronic heart assist blood pump in accordance with the patient's timy-varying physiological requirements, comprising the steps of:

a) periodically incrementing pump speed;

b) detecting the imminence of ventricular collapse;

c) decrementing pump speed by a predetermined amount whenever said imminence is detected;

d) said detecting step including:

i) measuring the current drawn by the motor of said blood pump;

ii) continually computing a spectral analysis representation of said current in the form of a Fourier series; and iii) providing a detection indication when the amplitude of the second harmonic term of said Fourier series exceeds a predetermined level.

8. A method of automatically controlling the speed of a continuously driven implanted electric chronic heart assist blood pump in accordance with the patient's timy-varying physiological requirements, comprising the steps of:

a) periodically incrementing pump speed;

b) detecting the imminence of ventricular collapse;

c decrementing pump speed by a predetermined amount whenever said imminence is detected;

d) said detecting step including:

i) measuring the current drawn by the motor of said blood pump;

ii) averaging said current; and iii) providing a detection indication when said current exceeds a predetermined level above said average.

9. A method for detecting an insufficient blood flow rate through an implanted continuously driven electric blood pump having an automatic speed control system, comprising the steps of:

a) measuring the current drawn by the motor of said blood pump;

b) computing the blood flow rate from only said measured current and the speed of said pump; and c) providing an indication when said computed blood flow rate falls below a predetermined minimum value.

10. The method of claim 9, in which said pump speed is responsive to a speed setpoint signal, and said flow rate is computed by the formula $$Q = \frac{\frac{3}{2}K_B I - B\omega - \left(a_0 \omega^3 + J\frac{d\omega}{dt}\right)}{a_1 \omega^2}$$

wherein Q is the flow rate; I is the motor current; $\omega$ is the pump speed; and $K_B$, B, J, $a_0$ and $a_1$ are constants associated with said pump motor.

11. A system for automatically controlling chronic heart assistance in accordance with a patient's physiological assist needs, comprising:

a) an implanted continuously driven electric blood pump whose current draw varies with load for a constant motor speed, comprising:

b) a speed control arranged to maintain said motor speed at a setpoint level determined by a setpoint signal; and c) a microprocessor arranged to periodically compute an optimum value of said setpoint signal as a function of the patient's physiological needs, said computation being done only on the basis of said current draw as the single variable input to said microprocessor.

12. The system of claim 11, in which said periodic setpoint signal computation is performed substantially every ten seconds.

13. The system of claim 11, in which said periodic setpoint signal computation is performed substantially every dozen heart beats of the patient.

14. The system of claim 11, in which said microprocessor is further arranged to compute a value representative of flow rate, said value being computed from said current draw.

15. The system of claim 11, in which said microprocessor is further arranged to maintain said setpoint level within a range delimited at its lower end by a predetermined minimum blood flow rate through said blood pump, and at its upper end by ventricular suction occurring at diastole.

16. The system of claim 11, in which said flow rate value is computed from said current draw by the formula $$Q = \frac{\frac{3}{2}K_B I - B\omega - \left(a_0 \omega^3 + J\frac{d\omega}{dt}\right)}{a_1 \omega^2}$$

wherein Q is the flow rate; I is the motor current; $\omega$ is the pump speed; and $K_B$, B, J, $a_0$ and $a_1$ are constants associated with said pump.

17. The system of claim 11, in which said microprocessor is further arranged to periodically compute said optimum setpoint signal by iteratively incrementing said setpoint signal until the imminence of a ventricular collapse condition of the patient is detected, and then decrementing said setpoint signal by a predetermined amount.

18. The system of claim 17, in which said microprocessor detects said imminent ventricular collapse condition by
   i) measuring said current draw;
   ii) computing from said current draw a value representative of blood flow rate;
   iii) computing the derivative of said blood flow rate with respect to said setpoint signal as said setpoint signal is incremented; and
   iv) providing a detection indication when said derivative drops below a predetermined value.

19. A system for automatically controlling chronic heart assistance in accordance with a patient's physiological assist needs, comprising:

a) a speed control arranged to maintain said motor speed at a setpoint level determined by a setpoint signal; and b) a microprocessor arranged to periodically compute an optimum value of said setpoint signal as a function of the patient's physiological needs, said computation being done on the basis of said current draw as the single variable input to said microprocessor;

c) said microprocessor detecting said imminent ventricular collapse condition by:
   i) measuring the current drawn by the motor of said blood pump;
   ii) continually computing a spectral analysis representation of said current; and
   iii) providing a detection indication when the amplitude of the second harmonic term of said spectral analysis representation exceeds a predetermined level.

20. A system for automatically controlling chronic heart assistance in accordance with a patient's physiological assist needs, comprising:

a) a speed control arranged to maintain said motor speed at a setpoint level determined by a setpoint signal; and b) a microprocessor arranged to periodically compute an optimum value of said setpoint signal as a function of the patient's physiological needs, said computation being done on the basis of said current draw as the single variable input to said microprocessor;

c) said microprocessor detecting said imminent ventricular collapse condition by:
   i) measuring the current drawn by the motor of said blood pump;
   ii) averaging said current; and
   iii) providing a detection indication when said current exceeds a predetermined level above said average.

21. In an implanted electrical blood pump continuously driven by a brushless DC motor, a method of determining the blood flow through said pump when pump speed and motor current are the only continuously ascertainable variable parameters, comprising the steps of:

a) producing a first signal representative of said pump speed;

b) producing a second signal representative of said motor current; and c) determining said blood flow from said signals by iteratively computing, in real time, the relationship $$Q = \frac{\frac{3}{2}K_B I - B\omega - \left(a_0 \omega^3 + J\frac{d\omega}{dt}\right)}{a_1 \omega^2}$$

wherein Q is the flow rate; I is the motor current; $\omega$ is the pump speed; and $K_B$, B, J, $a_0$ and $a_1$ are constants associated with said pump.

22. In combination with an implantable electric blood pump continuously driven by a brushless DC motor, a microprocessor arranged to iteratively compute the blood flow rate through said pump as a function of pump speed and motor current according to the formula $$Q = \frac{\frac{3}{2}K_B I - B\omega - \left(a_0 \omega^3 + J\frac{d\omega}{dt}\right)}{a_1 \omega^2}$$

wherein Q is the flow rate; I is the motor current; $\omega$ is the pump speed; and $K_B$, B, J, $a_0$ and $a_1$ are constants associated with said pump and motor.

* * * * *

UNITED STATES PATENT AND TRADEMARK OFFICE
CERTIFICATE OF CORRECTION

| | | |
|---|---|---|
| PATENT NO. | : 5,888,242 | Page 1 of 1 |
| APPLICATION NO. | : 08/740749 | |
| DATED | : March 30, 1999 | |
| INVENTOR(S) | : Seongjin Choi et al. | |

It is certified that error appears in the above-identified patent and that said Letters Patent is hereby corrected as shown below:

At Column 1, immediately following the title, please insert the following paragraph:

--STATEMENT AS TO FEDERALLY SPONSORED RESEARCH
Funding for the work described herein was provided in part by the National Institutes of Health, Grant Nos. NO1-HV-58155. The federal government may have certain rights in the invention.--

Signed and Sealed this

Twentieth Day of February, 2007

JON W. DUDAS
*Director of the United States Patent and Trademark Office*